United States Patent
Barnette et al.

[11] Patent Number: 5,928,881
[45] Date of Patent: Jul. 27, 1999

[54] METHOD OF IDENTIFYING AGONISTS AND ANTAGONIST FOR CC-CKR5 RECEPTOR

[75] Inventors: Mary S. Barnette, West Chester; Mary Ellen Brawner, Berwyn, both of Pa.

[73] Assignee: SmithKline Beecham Corporation, Philadelphia, Pa.

[21] Appl. No.: 08/890,336

[22] Filed: Jul. 11, 1997

Related U.S. Application Data

[60] Provisional application No. 60/021,534, Jul. 11, 1996, and provisional application No. 60/029,054, Oct. 24, 1996.

[51] Int. Cl.$^6$ .............................. C12Q 1/68; G01N 33/53; G01N 33/566
[52] U.S. Cl. .............................. 435/7.21; 435/6; 435/7.1; 435/7.2; 436/501
[58] Field of Search .................................. 435/6, 7.1, 7.2, 435/7.21; 436/501

[56] References Cited

FOREIGN PATENT DOCUMENTS

WO 9639437  12/1996  WIPO .......................... C07K 14/705

OTHER PUBLICATIONS

Combadiere et al., "Cloning and functional expression of a human eosimophil CC chemokine receptor", *The Journal of Biological Chemistry*, 270, pp. 16491–16494 (Dec. 15, 1995).

Carol J. Raport, J. Gosling, Vicki L. Schweickart, Patrick W. Gray, and Isreal F. Charo; *Molecular Cloning and Functional Characterization of a Novel Human CC Chemokine Receptor (CCR5) for RANTES, MIP–1β, MIP–1α*; Journal of Biological Chemistry; vol. 271, No. 29, Jul. 19, 1996; pp. 17161–17166.

Ghalib Alkhatib, Christophe Combadiere, C.C. Broder, Yu Feng, P.E. Kennedy, P.M. Murphy and E.A. Berger; *CC CKR5; A RANTES, MIP–1α, MIP–1β Receptor as a Fusion Cofactor for Macrophage–Tropic HIV–1*; Science; vol. 272; Jun. 28, 1996; pp. 1955–1958.

Michael Samson, Olivier Labbe, Catherine Mollereau, Gilbert Vassart and Marc Parmentier; *Molecular Cloning and Functional Expression of a New Human CC–Chemokine Receptor Gene*; Biochemistry; vol. 35, No. 11, 1996; pp. 3362–3367.

Christophe Combadiere, Sunil K. Ahuja and Philip M. Murphy; *Cloning and Functional Expression of a Human Eosinophil CC Chemokine Receptor*; Jouranl of Biological Chemistry; vol. 270, No. 27, Jul. 14, 1995; pp. 16491–16494.

David N. Leff; *Second HIV Cofactor Discovery In Six Weeks Advances Basis For Drug Development;* Bioworld Today–The Daily Biotechnology Newspaper; vol. 7, No. 122; Jun. 21, 1996.

*Primary Examiner*—John Ulm
*Attorney, Agent, or Firm*—William T. Han; William T. King; Charles M. Kinzig

[57] ABSTRACT

The invention provides a method of screening compounds to identify those which enhance or block the action of CC-CKR5. Further provided are compounds which blcok (antagonists) or enhance (agonists) the action of CC-CKR5.

8 Claims, No Drawings

METHOD OF IDENTIFYING AGONISTS AND ANTAGONIST FOR CC-CKR5 RECEPTOR

REFERENCE TO FIRST APPLICATION

This application claims the benefit of U.S. Provisional Application Ser. No. 60/021,534, filed Jul. 11, 1996, and U.S. Provisional Application Ser. No.60/029,054, filed Oct. 24, 1996.

BACKGROUND OF THE INVENTION

T cells are not only key regulators of the immune response to infectious agents but are critical for the initiation and maintenance of the inflammatory reaction in a variety of chronic diseases. Increased numbers or an enhanced activation state of T cells, especially CD4+ T cells, have been demonstrated in the synovium of individuals with rheumatoid arthritis (M. J. Elliott and R. N. Maini. *Int. Arch. Allergy Immunol.* 104:112–1125, 1994), in the bronchial mucosa of asthmatics (C. J. Corrigan and A. B. Kay. *Immunol. Today* 13:501–506, 1992), in the lesions of multiple sclerosis (R. Martin and H. F. McFarland. *Crit. Rev. Clin. Lab. Sci.* 32:121–182, 1995), in psoriatic lesions (J. L. Jones, J. Berth-Jone, A. Fletcher and P. E. Hutchinson. J. Pathol. 174:77–82, 1994) and in the fatty streaks of atherosclerosis (R. Ross. *Annu. Rev. Physiol.* 57:791–804, 1995). An understanding of the mechanisms behind the recruitment and activation of T cells into these tissues may lay the groundwork for novel therapeutic approaches to the treatment of these chronic inflammatory diseases.

T cells, as well as other inflammatory cells, migrate into tissues in response to the production of a variety chemotactic factors. Among these factors are members of a superfamily of 8–12 kDa proteins known as the chemokines (M. Baggiolini, B. Dewald, and B. Moser. *Adv. Immunol.* 55:97–179, 1994; J. J. Oppenheim, C. O. C. Zachariae, N. Mukaida, and K. Matsushima. *Annu. Rev. Immunol.* 9:617–648, 199 1). These proteins share common structural feature such as the presence of 3 or 4 conserved cysteine residues (M. Baggiolini, B. Dewald, and B. Moser. *Adv. Immunol.* 55:97–179, 1994; J. J. Oppenheim, C. O. C. Zachariae, N. Mukaida, and K. Matsushima. *Annu. Rev. Immunol.* 9:617–648, 199 1). RANTES or Regulated upon Activation Normal T cell Expressed and Secreted is a key member of CC branch of the chemokine family (M. Baggiolini, B. Dewald, and B. Moser. *Adv. Immunol.* 55:97–179, 1994; J. J. Oppenheim, C. O. C. Zachariae, N. Mukaida, and K. Matsushima. *Annu. Rev. Immunol.* 9:617–648, 199 1). The CC branch is defined by the absence of an intervening amino acid residue between the first two cysteine residues. The members of this family predominately elicit the migration of mononuclear cells, eosinophils and basophils (M. Baggiolini, B. Dewald, and B. Moser. *Adv. Immunol.* 55:97–179, 1994; J. J. Oppenheim, C. O. C. Zachariae, N. Mukaida, and K. Matsushima. *Annu. Rev. Immunol.* 9:617–648, 199 1). Although it is unlikely that a single chemokine mediates solely the recruitment of inflammatory cells into a lesion, RANTES is a key chemokine in the inflammatory reaction of chronic diseases as arthritis and asthma.

RANTES was originally identified as gene product induced late after antigen activation of T-cells (T. J. Schall, J. Jongstra, B. J. Dyer, J. Jorgensen, et al. *J. Immunol.* 141:1018–1025, 1988). More recently, RANTES has been shown to be synthesized and secreted by a diverse group of cells that include epithelial and endothelial cells (C. Stellato, L. A. Beck, G. A. Gorgone, D. Proud, et al. *J. Immunol.* 155:410–418, 1995; O. A. Marfaing-Koka, O. Devergne, G. Gorgone, A. Portier, et al. *J. Immunol.* 154:18701878, 1994), synovial (P. Rathanaswanai, M. Hachicha, M. M. Sadick, T. J. Schall, et al. *J. Biol. Chem.* 268:5834–5839, 1993) and dermal fibroblasts (M. Sticherling, M. Kupper, F. Koltrowitz, E. Bomscheuer, et al. *J. Invest. Dermatol.* 105:585–591, 1995), mesangial cells (G. Wolf, S. Aberle, F. Thaiss, et al. *Kidney Int.* 44:795–804, 1994) and platelets (Y. Koameyoshi, A. Dorschner, A. I. Mallet, E. Christophers, et al. *J. Exp. Med.* 176:587–592, 1992). In these cells RANTES mRNA is rapidly upregulated in response to IL-1 or TNFα. Although RANTES mRNA is not usually detected in normal tissues (J. M. Pattison, P. J. Nelson and A. M. Krensky. *Clin. Immunother.* 4:1–8, 1995), increased mRNA or protein is present in diseases characterized by a mononuclear infiltrate. For example, RANTES mRNA was visualized using in situ hybridization in renal allografts undergoing rejection (J. M. Pattison, P. J. Nelson and A. M. Krensky. *Clin. Immunother.* 4:1–8, 1995; K. C. Nadeau, H. Azuma and N. I. Tilney. *Proc. Natl. Acad. USA* 92:8729–8733, 1995), in the skin of atopic dermatitis patients after exposure to antigen (S. Ying, L. Taborda-Barata, Q. Meng, M. Humbert, et al. *J. Exp. Med.* 181:2153–2159, 1995), and in endothelial cells of coronary arteries undergoing accelerated atherosclerosis after cardiac transplant (J. M. Pattison, P. J. Nelson and A. M. Krensky. *Clin. Immunother.* 4:1–8, 1995). Increased immunoreactive protein for RANTES is present in bronchoalveolar lavage fluid (R. Alam, J. York, M. Boyers, et al. *Am. J. Resp. Crit. Care Med.* 149:A951, 1994) and sputum from asthmatic individuals (C. M. Gelder, P. S. Thomas, D. H. Yates, I. M. Adcock, et al. Thorax 50:1033–1037, 1995).

Samson has recently described a new CC-chemokine receptor called hChem R13 (CC-CKR5). M. Samson, Biochemistry 35, 3362–3367 (1996). We have now demonstrated that RANTES is a ligand for CC-CKR5.

SUMMARY OF THE INVENTION

The present invention provides a method of screening compounds to identify those which enhance or block the action of CC-CKR5 using RANTES. Further provided are compounds which block (antagonists) or enhance (agonists) the action of CC-CKR5; such compounds are useful for treatmenting AIDS, rheumatoid arthritis, asthma, multiple sclerosis, psoriatic lesions, artherosclerosis, and other inflammatory disease.

DETAILED DESCRIPTION

We have now discovered that hChem R13 (CC-CKR5) is a receptor for RANTES. Thus the present invention provides a method of screening compounds which enhance (agonists) or block (antagoinsts) the action of CC-CKR5. Further provided are compounds which block (antagonists) or enhance (agonists) the action of CC-CKR5.

In general, such screening procedures involve providing appropriate cells which express the CC-CKR5 on the surface thereof. In particular, a polynucleotide encoding CC-CKR5 is employed to transfect cells to thereby express the CC-CKR5 receptor on the surface thereof. Such transfection can be accomplished by procedures standard in the art. See for example, Sambrook et al., *MOLECULAR CLONING, A LABORATORY MANUAL,* 2nd Ed.; Cold Spring Harbor Laboratory Press, Cold Spring Harbor, N.Y. (1989).

One such screening procedure involves the use of melanophores which are transfected to express the CC-CKR5 receptor of the present invention. Such a screening technique is described in PCT WO 92/01810 published Feb. 6, 1992, which is herein incorporated by reference.

Thus, for example, such assay may be employed for screening for a receptor antagonist by contacting the melanophore cells which encode the CC-CKR5 receptor with both the RANTES and a compound to be screened. Inhibition of the signal generated by the ligand indicates that a compound is a potential antagonist for the receptor, i.e., inhibits activation of the receptor.

The screen may be employed for determining an agonist by contacting such cells with compounds to be screened and determining whether such compound generates a signal, i.e., activates the receptor to stimulate the accumulation of cAMP.

Other screening techniques include the use of cells which express the CC-CKR5 receptor (for example, transfected CHO cells, RBL-2 cells or other mammalian cells) in a system which measures extracellular pH changes caused by receptor activation, for example, as described in Science, volume 246, pages 181–296 (October 1989), herein incorporated by reference. For example, potential agonists or antagonists may be contacted with a cell which expresses the CC-CKR5 receptor and a second messenger response, e.g. signal transduction or pH changes, or making use of a reporter gene system, for example luciferase, may be measured to determine whether the potential agonist or antagonist is effective.

Another such screening technique involves introducing mRNA encoding the CC-CKR5 receptor into Xenopus oocytes, RBL-2 or other mammalian cells to transiently express the receptor. The cells with the expressed receptor may then be contacted in the case of antagonist screening with RANTES and a compound to be screened, followed by detection of inhibition of a calcium or cAMP signal, or in the case of an agonist, by detection of stimulation of a calcium or cAMP signal.

Another screening technique involves expressing the CC-CKR5 receptor in which the receptor is linked to a phospholipase C or D. As representative examples of such cells, there may be mentioned endothelial cells, smooth muscle cells, embryonic kidney cells, etc. The screening for an antagonist or agonist may be accomplished as hereinabove described by detecting activation of the receptor or inhibition of activation of the receptor from the phospholipase second signal.

Another method involves screening for CC-CKR5 receptor inhibitors by determining inhibition of binding of labeled RANTES to cells or membranes which have the receptor on the surface thereof. Such a method involves transfecting a eukaryotic cell, such as CHO or RBL-2 cell, with DNA encoding the CC-CKR5 receptor such that the cell expresses the receptor on its surface and contacting the cell with a potential antagonist in the presence of a labeled form of RANTES. The RANTES can be labeled, e.g., by radioactivity. The amount of labeled ligand bound to the receptors is measured, e.g., by measuring radioactivity accociated with transfected cells or membrane from these cells. If the potential antagonist binds to the receptor, as determined by a reduction of labeled ligand which binds to the receptors, the binding of labeled ligand to the receptor is inhibited.

Another method involves screening for CC-CKR5 inhibitors by determining inhibition or stimulation of CC-CKR5-mediated cAMP and/or adenylate cyclase accumulation or diminution. Such a method involves transfecting a eukaryotic cell, such as CHO or RBL-2 cell, with CC-CKR5 receptor to express the receptor on the cell surface. The cell is then exposed to potential antagonists in the presence of RANTES. The amount of cAMP accumulation is then measured. If the potential antagonist binds the receptor, and thus inhibits CC-CKR5 binding, the levels of CC-CKR5-mediated cAMP, or adenylate cyclase, activity will be reduced or increased.

The present invention also provides a method for determining whether a ligand not known to be capable of binding to the CC-CKR5 receptor can bind to such receptor which comprises contacting a mammalian cell which expresses the CC-CKR5 receptor with RANTES under conditions permitting binding of ligands to the CC-CKR5 receptor, detecting the presence of a ligand which binds to the receptor and thereby determining whether the ligand binds to the CC-CKR5 receptor. The systems hereinabove described for determining agonists and/or antagonists may also be employed for determining ligands which bind to the receptor.

In general, agonists for CC-CKR5 receptors are employed for therapeutic purposes, such as the treatment of AIDS, rheumatoid arthritis, asthma, multiple sclerosis, psoriatic lesions, artherosclerosis, and other inflammatory disease.

Antagonists for CC-CKR5 receptors may be employed for a variety of therapeutic purposes. For example, such antagonists are to be employed for treatment of AIDS, rheumatoid arthritis, asthma, multiple sclerosis, psoriatic lesions, artherosclerosis, and other inflammatory disease.

Examples of potential CC-CKR5 receptor antagonists are an antibody, or in some cases an oligonucleotide, which binds to the G-protein coupled receptor but does not elicit a second messenger response such that the activity of the G-protein coupled receptor is prevented.

Potential antagonists also include proteins which are closely related to the ligand of the CC-CKR5 receptor, i.e. a fragment of the ligand, which have lost biological function and when binding to the CC-CKR5 receptor, elicit no response.

Another potential antagonist is a small molecule which binds to the CC-CKR5 receptor, making it inaccessible to ligands such that normal biological activity is prevented. Examples of small molecules include, not limited to small peptides or peptide-like molecules, organic molecules.

Potential antagonists also include a soluble form of CC-CKR5 receptor, e.g. a fragment of the receptor, which binds to RANTES and prevents RANTES from interacting with the membrane bound CC-CKR5 receptor.

The CC-CKR5 antagonists or agonists, may be employed in combination with a suitable pharmaceutical carrier. Such compositions comprise a therapeutically effective amount of the antagonist or agonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the topical, intravenous, intraperitoneal, intramuscular, intranasal or intradermal routes. The pharmaceutical compositions are administered in an amount which is effective for treating and/or prophylaxis of the specific indication. In general, the pharmaceutical compositions will be administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

This invention further provides a method of screening drugs or identifying drugs which specifically interact with, and bind to, the human CC-CKR5 receptor polypeptide on the surface of a cell which comprises contacting a mammalian cell comprising an isolated DNA molecule encoding the CC-CKR5 receptor with a plurality of drugs, determining those drugs which bind to the mammalian cell, and thereby identifying drugs which specifically interact with and bind to a CC-CKR5 receptor polypeptide.

EXAMPLES

Expression Cell Lines

The coding region for CC-CKR5 was amplified by PCR using a 5' specfic oligonucleotide(GCACAGG AAGCTTCAAGATGGATTATCAAGTGTCAAG), SEQ ID NO: 1, and a 3' oligonucleotide (5'-CCAGCCCACTT GGATCCGTGTCACAAGCCCAC), SEQ ID NO: 2, containing HindIII and BamHI restriction sites respectively. The 1.0 kb fragment was digested with HindIII and BamHI and inserted into the mammalian expression vector pCDN (Aiyar, N., Baker, E., Wu, H.-L, Nambi, P., Edwards, R. M., Trill, J. T., Ellis, C. and Bergsma, D. J. (1994) *Human AT1 receptor is a single copy gene: characterization in a stable cell line.* Mol. Cell Biochem. 131:75.) that had been digested with HindIII and BamHI. The insert of the resulting construct was completely sequenced to confirm its identity and oreintation.

pCDN:CC-CKR5 was electroporated into chinese hamster ovary cells (Potter, H., Weir, L., and Leder, P. (1984). Enhancer-dependent expression of human kappa immunoglobulin genes introduced into mouse pre-B lymphocytes by electroporation. Proc. Natl. Acad. Sci. USA 81:7161.) or RBL-2 (DeMartino, J. A., Van Piper, G., Sicilino, S. J., Molineaux, C. J., Konteatis, Z. D., Rosen, H., and Springer, M. S. (1994) J. Biol. Chem. 269:14446.). Stably transfected CHO cell lines were isolated by growing cells in the absence of nucleosides, while stable RBL-2 cell lines were isolated by their ability to grow in the presence of 400 microgram per ml of G418. Stable clones that expressed CC-CKR5 were identified by their ability to bind labelled RANTES at high affinity using membrane binding assays.

Assay Development

A. Binding

A 96 well filtration assay was established to measure the binding of $^{125}$RANTES to whole CHO cells expressing the CC-CKR5 and to CHO cell membranes. Briefly, cells (~0.5–1.0×10$^6$ cells/ml) are suspended in RPMI 1640 media with 0.05% NaN3 and 0.1% BSA. These are incubated in the absence or presence of chemokines and 0.3–0.6 nM $^{125}$I-RANTES in a total volume of 0.2 ml. The cells are incubated for a period of 45–90 min at room temperature and the assay terminated by filtration onto GF/C filters pretreated with polyethylene imine. These filters are washed ~12 times with PBS containing 0.08% BSA and 0.05% NaN. The bound radioactivity is determined by liquid scintillation spectormetery. Non-specific binding averages between 25–30% of total binding. For CHO cell membranes, the assay is essentially the same except that membranes are suspended in Tris buffer (50 mM Tris, pH 7.4; 1 mMCaC12, 5 mM MgC12; ; 0.1% BSA) rather than RPMI 1640. The samples are incubated at room temperature for 45 min and the assay terminated by filtration through GF/C filters. The average non-specific binding ranges from 30–50% of total binding.

The binding study can be carried out using RBL-2 cells using susbtantially the same protocol as above.

B. Functional

To characterize the functional response of this receptor and to verify any leads for receptor antagonists, the following two systems are used. The first examines the ability of RANTES and other chemokines to elicit a $Ca^{+2}$ signal in CHO, RBL-2 or other mammalian cells expressing the CC-CKR5 receptor by measuring the increased fluorescence of Fura-2. The second system examines the ability of RANTES and other chemokines to produce an acidification of the extracellular medium after activation of the cells as measured by a microphysiometer.

What is claimed is:

1. A method for identifying compounds which bind to and activate the CC-CKR5 receptor comprising:

contacting a cell expressing on the surface thereof CC-CKR5 receptor, said receptor being associated with a second component capable of providing a detectable signal in response to the binding of RANTES to said receptor, with a compound to be screened under conditions to permit binding to the receptor; and determining whether the compound binds to and activates the interaction of RANTES and CC-CKR5 receptor by detecting the presence or absence of a signal generated from the interaction of RANTES and CC-CKR5 receptor.

2. A method of claim 1 in which a cell expressing CC-CKR5 receptor is RBL-2 or CHO cell.

3. A method for identifying compounds which bind to and inhibit the CC-CKR5 receptor comprising:

in the presence of RANTES, contacting a cell expressing on the surface thereof CC-CKR5, said receptor being associated with a second component capable of providing a detectable signal in response to the binding of RANTES to said receptor, with a compound to be screened under conditions to permit binding to the receptor; and determining whether the compound binds to and inhibits the interaction of RANTES and CC-CKR5 receptor by detecting the presence or absence of a signal generated from the interaction of the RANTES and CC-CKR5 receptor.

4. A method of claim 3 in which a cell expressing CC-CKR5 receptor is RBL-2 or CHO cell.

5. A method of screening for CC-CKR5 receptor inhibitor (antagonist) comprising the steps of:

(a) incubating a labeled RANTES with a whole cell expressing CC-CKR5 receptor on the cell surface, or cell membrane containing CC-CKR5 receptor;

(b) measuring the amount of labeled RANTES bound to the whole cell or the cell membrane;

(c) adding a candidate compound to a mixture of labeled RANTES and the whole cell or the cell membrane of step (a) and allowing to attain equilibrium;

(d) measuring the amount of labeled RANTES bound to the whole cell or the cell membrane after step (c); and (e) comparing the difference in the labeled RANTES bound in step (b) and (d), such that the compound which causes the reduction in binding in step (d) is an inhibitor.

6. The method of claim 5 in which the receptor is on the surface of the cell.

7. The method of claim 5 in which the receptor is in the cell membrane.

8. The method of claim 6 in which the cell is CHO or RBL-2 cell.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 37 base pairs
      (B) TYPE: nucleic acid
      (C) STRANDEDNESS: single
      (D) TOPOLOGY: linear (xi) SEQUENCE DESCRIPTION: SEQ ID NO:1:

GCACAGGAAG CTTCAAGATG GATTATCAAG TGTCAAG      37

(2) INFORMATION FOR SEQ ID NO:2:

```
      (i) SEQUENCE CHARACTERISTICS:
          (A) LENGTH: 32 base pairs
          (B) TYPE: nucleic acid
          (C) STRANDEDNESS: single
          (D) TOPOLOGY: linear (xi) SEQUENCE DESCRIPTION: SEQ ID NO:2:

CCAGCCCACT TGGATCCGTG TCACAAGCCC AC                                          32
```